(12) United States Patent
Stein et al.

(10) Patent No.: US 10,744,218 B2
(45) Date of Patent: Aug. 18, 2020

(54) HOLDER FOR DISINFECTION OF TONOMETER TIPS OR THE LIKE AND METHOD OF USE

(71) Applicant: United States Government as Represented by The Department of Veterans Affairs, Washington, DC (US)

(72) Inventors: Richard A. Stein, Leawood, KS (US); Kelly R. Foudray, Leavenworth, KS (US)

(73) Assignee: United States Government as Represented by the Department of Veterans Affairs, Washington, DC (US)

( * ) Notice: Subject to any disclaimer, the term of this patent is extended or adjusted under 35 U.S.C. 154(b) by 325 days.

(21) Appl. No.: 15/538,844

(22) PCT Filed: Dec. 18, 2015

(86) PCT No.: PCT/US2015/066925
§ 371 (c)(1),
(2) Date: Jun. 22, 2017

(87) PCT Pub. No.: WO2016/106156
PCT Pub. Date: Jun. 30, 2016

(65) Prior Publication Data
US 2017/0304479 A1    Oct. 26, 2017

Related U.S. Application Data

(60) Provisional application No. 62/095,228, filed on Dec. 22, 2014.

(51) Int. Cl.
*A61B 50/00*    (2016.01)
*A61B 50/20*    (2016.01)
(Continued)

(52) U.S. Cl.
CPC ............... *A61L 2/26* (2013.01); *A61B 50/00* (2016.02); *A61B 50/20* (2016.02); *A61B 50/22* (2016.02);
(Continued)

(58) Field of Classification Search
CPC ........... A61L 2/26; A61B 50/00; A61B 50/20; A61B 50/22; B08B 3/045
See application file for complete search history.

(56) References Cited

U.S. PATENT DOCUMENTS 4,772,418 A    9/1988  Leoncavallo
5,053,207 A  * 10/1991  Lervick ..................... A61L 2/18
                                              422/300

(Continued)

FOREIGN PATENT DOCUMENTS

WO    2011-112998 A2    1/1991

OTHER PUBLICATIONS

International Search Report and Written Opinion. PCT/US2015/066925. dated Apr. 6, 2016. 11 pages.

*Primary Examiner* — Sean E Conley
(74) *Attorney, Agent, or Firm* — Ballard Spahr LLP

(57) ABSTRACT

A holder device for holding a plurality of tonometer tips or the like during a disinfection procedure has a top wall, spaced rims extending downward from the top wall to engage a support surface and hold the top wall above the support surface, and handle portions extending upwards from the top wall. The top wall has a plurality of spaced holes of predetermined diameter each configured to hold a tip extending partially through the hole with a lower end of the tip spaced above a support surface. A cover plate is releasably secured between the handle portions at a location spaced above the top wall after loading the holes with tips, (Continued)

and holds the tips in the holes while at least a major portion of the device is submerged in a bath of disinfectant.

9 Claims, 3 Drawing Sheets

(51) Int. Cl.
*A61B 50/22* (2016.01)
*A61L 2/26* (2006.01)
*B08B 3/04* (2006.01)
*A61L 2/18* (2006.01)
*A61B 3/16* (2006.01)

(52) U.S. Cl.
CPC ............... *B08B 3/045* (2013.01); *A61B 3/16* (2013.01); *A61L 2/18* (2013.01)

(56) References Cited

U.S. PATENT DOCUMENTS

| | | | | |
|---|---|---|---|---|
| 5,114,680 A | * | 5/1992 | Obermiller | B01L 9/06 211/74 |
| 5,409,667 A | * | 4/1995 | Elson | B01L 9/06 211/60.1 |
| 5,843,388 A | | 12/1998 | Arroyo et al. | |
| 6,251,686 B1 | * | 6/2001 | Studer | B01L 9/06 211/74 |
| 6,365,115 B1 | | 4/2002 | Wood | |

\* cited by examiner

HOLDER FOR DISINFECTION OF TONOMETER TIPS OR THE LIKE AND METHOD OF USE

BACKGROUND

Related Field

The subject matter discussed herein relates generally to sterilization or disinfection of medical equipment, and is particularly concerned with a holder or tray for holding tonometer prisms or tips and the like and a method of disinfection of medical instrument tips held in the holder.

Related Background

Ocular tonometry is a technique used by ophthalmologists and optometrists to check intraocular pressure in the eye and screen for various eye diseases and conditions, such as glaucoma, hyphema, traumatic damage and possible optic nerve issues. Intraocular pressure is measured by a tonometer which has prism or tip which touches the eye surface and measures force needed to flatten an area of the surface. After measuring intraocular pressure in one or both eyes, the tonometer tips or prisms are removed and must be disinfected before they can be used on the next patient. Disinfection typically consists of soaking in a disinfectant solution for a predetermined time period. After soaking, the tonometer tip must be rinsed.

Current commercial systems for disinfecting tonometer prisms or tips accommodate only limited numbers of tonometer tips at a time, and some accommodate only one tip. In some systems, one or two tips are placed in individual wells holding disinfectant solution. After disinfection, tips are often rinsed individually. This is quite time consuming, particularly in large ophthalmology centers where many tips may require disinfection every day.

SUMMARY

According to one aspect, a holder device is provided for holding tonometer tips or the like during disinfection or sterilization after use, such as prisms or tips of tonometers used for measuring eye pressure. In one aspect, the holder device has a top wall having a plurality of spaced holes of predetermined diameter configured to hold a tonometer tip extending partially through the hole, a base portion or rims extending downward from opposite sides or ends of the top wall to support the top wall and any tips held in the top wall at a position raised from a support surface, and spaced handle portions extending upwards from the top wall. A cover plate is releasably secured between the handle portions at a location spaced above the top wall and above any tonometer tips positioned in holes in the top wall.

In one aspect, the handle portions have opposing inner faces with aligned horizontal grooves extending across the faces at a predetermined height above the top wall, and the cover plate has opposite ends configured for releasable sliding engagement in the grooves once tips have been placed in the holes in the top wall for disinfection. The elevated sliding cover plate is positioned to stop the tips from floating up out of the holes when the tip holder is placed in a bath or container of disinfectant solution with the tips completely submerged. Once the tips have been soaked for a sufficient time period, the tip holder can be lifted from the disinfectant solution using the handles, and the tips can all be rinsed simultaneously via the open lower end and open front and back sides of the device while remaining on the plate. This is considerably more efficient than prior disinfection techniques where only a few tips are disinfected simultaneously and often have to be rinsed one at a time by hand.

In other embodiments, a similar holder may be designed with holes of different sizes or shapes to hold other small reusable medical items or tips of similar shape for simultaneous disinfection purposes. For example, the device could be used to clean Goldmann-style 3-mirror diagnostic lenses (or variations of diagnostic and laser lenses which have a similar design/shape, but smaller dimensions) which are cleaned in a bleach solution similar to tonometer tips and have a similar cone shape and would be conducive to cleaning in a device of similar design. The holder device is useful in any medical facility where numerous identical tonometer tips or other items of similar shape are used daily for diagnosis or treatment, allowing multiple such items to be disinfected simultaneously and reducing the time and staff needed for disinfection procedures.

Other features and advantages will become more readily apparent to those of ordinary skill in the art after reviewing the following detailed description and the accompanying drawings.

DETAILED DESCRIPTION

The subject matter described herein is taught by way of example implementations. Various details have been omitted for the sake of clarity and to avoid obscuring the subject matter. The examples shown and described below are directed to a holder device or tray for holding a plurality of medical tips or the like during disinfection and rinsing.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention.

Although the following description is directed to a tip holder device or tray for use in disinfecting tonometer prisms or tips, it will be understood that the holder device may be designed for simultaneous disinfection of other similar small, reusable devices used daily and in quantity in medical facilities, with appropriate adjustment of the dimensions. Although the tip holder or holder device is rectangular in the illustrated embodiment, it may be of other shapes in other embodiments, such as round or oval.

FIGS. 1 to 5 illustrate one embodiment of a tonometer prism or tonometer tip holder 10 for use in disinfection of multiple tonometer tips simultaneously. Tip holder or tip holder device 10 in the illustrated embodiment is designed to hold up to twenty four tonometer tips, but similar devices may be designed to hold a greater or a lesser number of tips.

Figure 1:
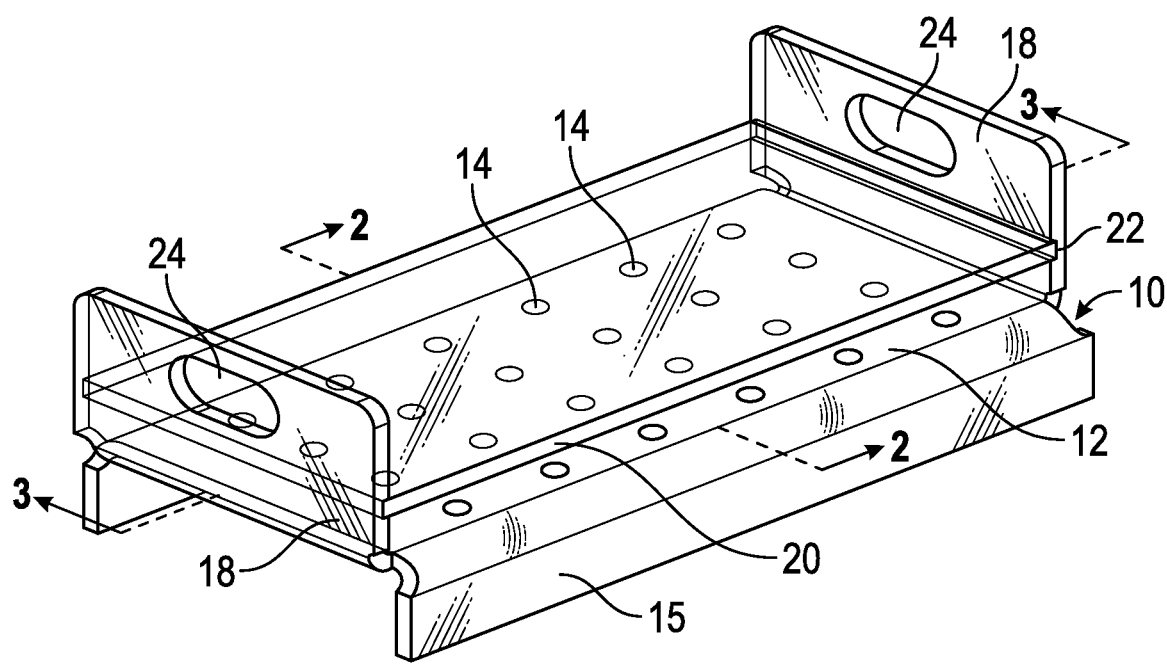
FIG. 1 is a perspective view of one embodiment of a tonometer tip holder for use in disinfection of tonometer tips.
Figure 2:
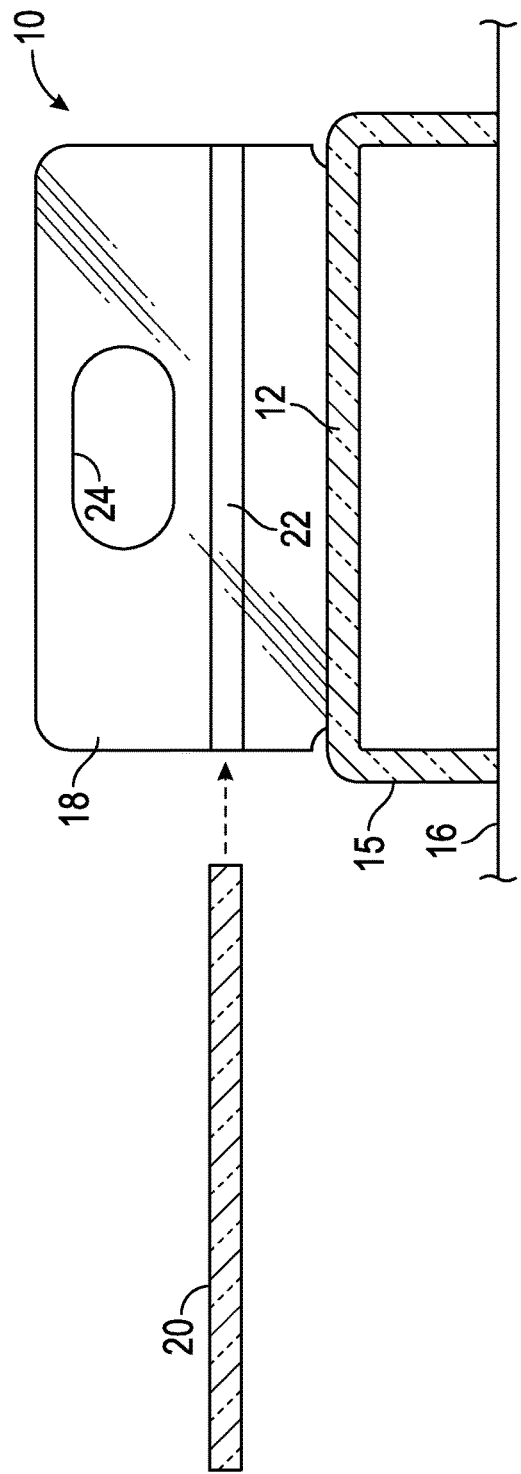
FIG. 2 is a cross-section on the lines 2-2 of FIG. 1, with the cover or plate shown separate from the remainder of the device and aligned with a receiving groove of one of the handle portions.
Figure 3:
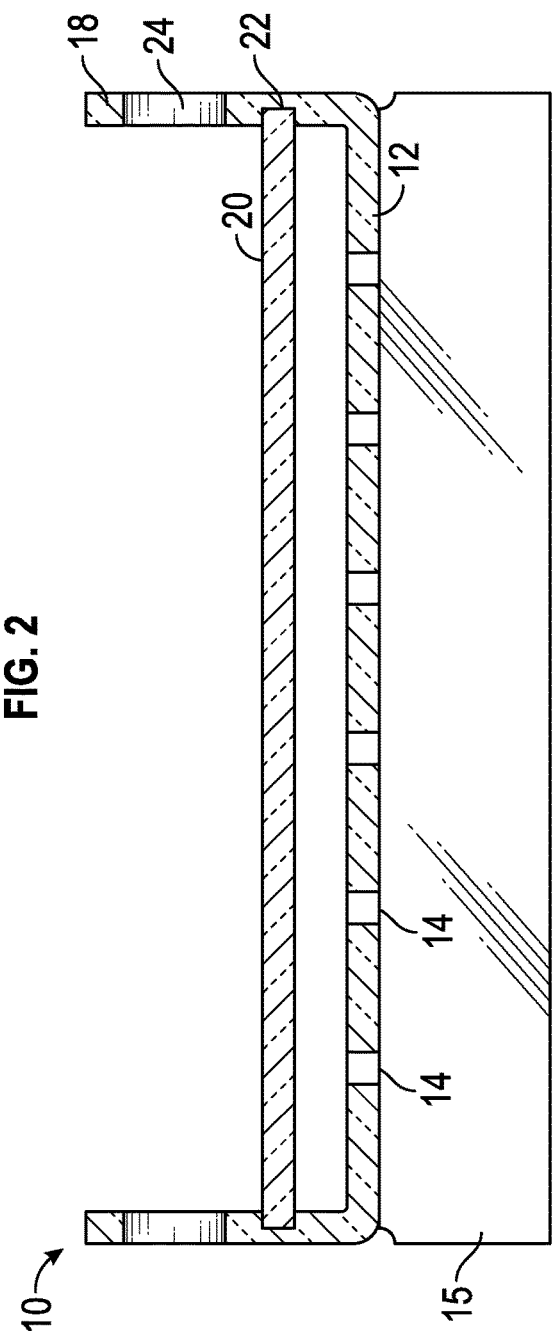
FIG. 3 is a cross-section on the lines 3-3 of FIG. 2 with the cover plate in position.

As best illustrated in FIGS. 1 to 3, tip holder 10 has a top wall 12 with a plurality of spaced holes 14, a base portion or spaced rims 15 extending downward from opposite sides of top wall 12 and designed to hold the wall at a predetermined spacing above a support surface 16 (FIG. 2), an upwardly extending handle portion 18 at each end of top wall 12, and a cover plate 20 configured for sliding engagement in opposing grooves 22 on the inner faces of handle portions 18. The cover plate is shown in position above the top wall in FIGS. 1 and 3 to 5, and separate from the device or tray in FIG. 2. Handle portions 18 also have cutouts or handle openings 24 for gripping by a user when moving the device from one location to another. As can be seen in the drawings, device 10 is completely open below the top wall and at each end to form a channel under the top wall 12, and is also open at the front and back between cover plate 20 and top wall 12. This allows disinfectant or rinse water to flow both under and over the top wall and completely cover tonometer tips when held in the device as seen in FIGS. 4 and 5.

The tip holder or tip holder device 10 may be made of any suitable material and in one example is made of clear plastic material, such as Plexiglas acrylic material. The top wall, base portion 15, and handle portions 18 may be made from one piece of plastic material, with the base portion comprising rims which are bent downwards on opposite sides of the top wall, and the handle portions being formed by bending up parts of the plastic at opposite ends of the top wall, after cutting out openings 15 to form handles or gripping portions. Aligned, inwardly facing grooves 22 for slidably receiving opposite ends of the plate are also cut into inner faces of handle portions 18 below openings 15. Holes 14 may be drilled into top wall 12 before or after the rims and handle portions are bent away from wall 12. Cover plate 20 comprises a flat rectangular plate of the same material as the remainder of the device and has a thickness slightly less than the height of grooves 22. Tip holder 10 can be scaled up in larger dimensions to accommodate and disinfect more tips at a time for larger clinics or ophthalmology centers, based on the total number of such tips generally used in one day.

The dimensions of device 10 are dependent on the dimensions of the tips to be held in the device during sterilization or disinfection and subsequent rinsing. In one embodiment, holder device 10 is designed to hold tonometer prisms or tips, such as tips for use with Goldmann applanation tonometry instruments, such as the Haag-Streit tonometer measuring prism or tip. In the illustrated embodiment, there are four rows of six holes each, i.e. a total of twenty four holes, but a greater or lesser number of holes may be provided in other embodiments with suitable scaling up and down of the device dimensions. Holder devices with different numbers of holes such as 12, 36, 48, or more may be provided. In one example, the tip holder device 10 was formed from acrylic plastic material of 5 mm thickness with twenty four holes of 7/16 inch (11 mm) diameter drilled out with a standard straight bit. In other embodiments, there may be any number of holes from ten to over one hundred, depending on how many tonometer tips are typically used in one day at a particular medical facility. The spacing between holes is sufficient to prevent tips from bumping into each other and potentially causing damage to their surfaces. One example of the device 10 of FIGS. 1 and 5 had a length of around 216 mm between opposite ends, and a width of around 115 mm between opposite sides. In one example, grooves 22 had a height of around 6 mm and a depth of around 4 mm, and were located around 16 mm above the top wall 12, while the lower surface of top wall 12 was raised around 26 mm from a support surface 16 when the rims 15 engaged a support surface.

Figure 4:
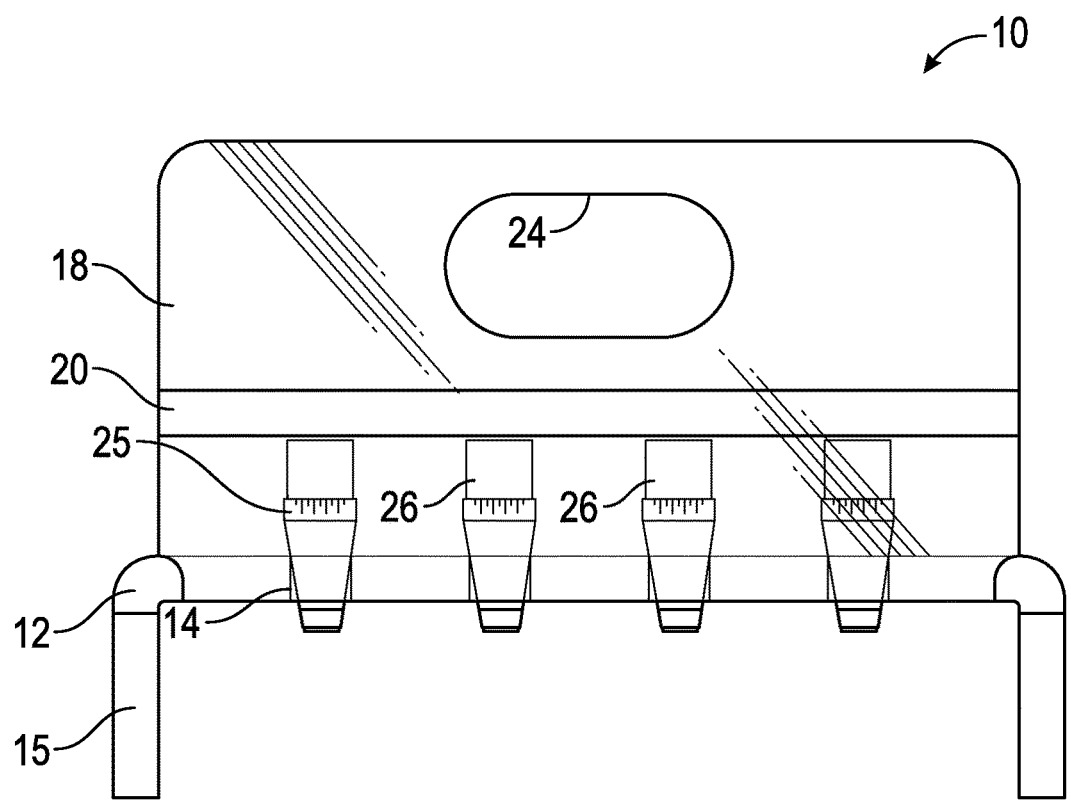
FIG. 4 is an end elevation view of the tip holder of FIGS. 1 to 3 on a larger scale than FIGS. 1 to 3, with tonometer tips held in the holes for disinfection purposes.
Figure 5:
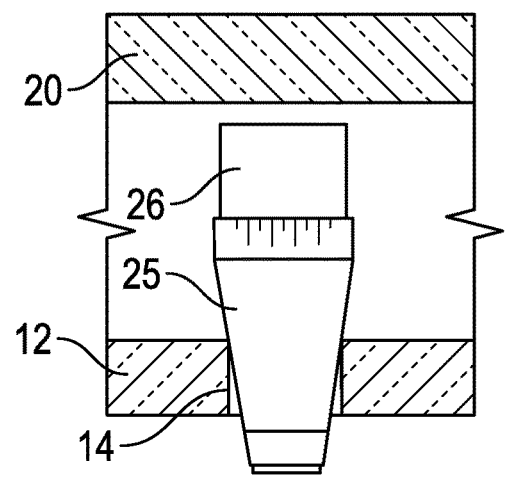
FIG. 5 is a cutaway view on a larger scale illustrating a tonometer tip held in one of the holes.

FIGS. 4 and 5 illustrate tonometer tips 26 engaged in holes 14 in top wall 12 of the device. The cover plate 20 is removed prior to loading tips to be cleaned and disinfected into holes 14. Once loading is completed, cover plate 20 is engaged in grooves 22 to extend over the upper ends of the loaded tips, as illustrated in FIGS. 4 and 5. The hole diameter is less than the diameter towards the upper end of the tapered portion 25 of the tip, so that the tip cannot fall through the hole but is a loose fit in the hole due to the taper. This allows disinfectant to flow into the hole and around the tip (see FIG. 5). The height of the top wall over the lower ends of rims along with the height of cover plate 20 over the top wall are selected so that the lower ends of tips engaged in holes 14 do not touch the support surface and the cover plate is either touching or a short distance above the top or upper ends of the tips, as illustrated in FIGS. 4 and 5. In one embodiment, cover plate 20 is spaced one or two millimeters above the top of tips 26 engaged in holes 14.

Once the tip holder or tray is loaded and the cover plate is in place above the loaded tips, the tip holder is lifted with the handles and placed into a bath or container of disinfectant solution with the solution completely covering the tips. The tips cannot float up due to cover plate 20 extending over all of the tips, which is an advantage over some prior art devices where tips floating up so they are partially out of the disinfectant solution can be a problem. Once the tips have been soaked in the disinfectant solution for a sufficient time period, the tip holder or tray is removed from the solution, again using the handles, and the tips are then rinsed thoroughly with water to remove the disinfectant or bleach. The cover stays in place during rinsing as the tips could otherwise float out of the holes and the wash needs to rinse the bleach off parts of the tonometer tips that are the most superior in the apparatus, as well as the lowermost ends of the tips. If desired, holes smaller than the tonometer tips may be provided in the cover plate to allow increased flow of water, but the open sides between the top wall and cover plate are normally sufficient to accommodate enough flow. Also, the step of making holes in the cover plate increases cost of production.

The tonometer tip holder described above can accommodate many more tonometer tips for disinfection than other available systems which typically only hold one to five tips. This allows multiple tips to be cleaned efficiently after use, considerably reducing tonometer tip cleaning times in busy ophthalmology centers. In other embodiments, a similar holder device may be designed with holes of different sizes or shapes and adjusted top wall height and elevated cover plate spacing to hold other small items or reusable medical devices having a similar shape to tonometer tips. For example, the device could be designed for cleaning of Goldmann-style 3-mirror diagnostic lenses (or variations of diagnostic and laser lenses which have a similar design/shape, but smaller dimensions) which are cleaned in bleach solution similar to tonometer tips and have a similar cone shape and would be conducive to cleaning in a device of similar design, but with larger holes and correct spacing of the inferior portion of the lens to the support surface below the top wall and a similarly elevated sliding plate to be above the superior edge of the lens. The holder device is useful in any medical facility where numerous identical small items or pieces of medical equipment such as tonometer tips or other items of similar shape are used daily for diagnosis or treatment, allowing multiple such items to be disinfected simultaneously and reducing the time and staff needed for disinfection procedures.

The foregoing systems and methods and associated devices are susceptible to many variations. Additionally, for clarity and concision, many descriptions of the systems and methods have been simplified.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter that is broadly contemplated by the present invention. It is further understood that the scope of the present invention fully encompasses other embodiments that may become obvious to those skilled in the art.

What is claimed is:

1. A holder device for holding a plurality of tonometer tips or items of similar shape requiring disinfection or sterilization after use, comprising:
    a top wall;
    a rim portion extending downward from the top wall by a first predetermined distance and configured to engage a support surface and hold the top wall in a raised position, wherein the raised position is above the support surface by the first predetermined distance;
    the top wall having a plurality of spaced holes of predetermined diameter configured to hold an item of medical equipment extending partially through the hole with a lower end of the item spaced above a support surface engaged by the rim portions;
    a pair of spaced handle portions extending upwards from the top wall; and
    a cover plate releasably secured between the handle portions at a location spaced a predetermined second distance above the top wall and configured for holding the items in the holes while at least a major portion of the device is submerged in a bath of disinfectant solution.

2. The device of claim 1, wherein the handle portions have opposing inner faces and each inner face has a horizontal groove extending across the inner face at a predetermined height above the top wall, and the cover plate has opposite ends configured for releasable sliding engagement in the grooves.

3. The device of claim 1, wherein the top wall has opposite sides and opposite ends, the handle portions extend upwards from opposite ends of the top wall, and the rim portion comprises a pair of rims extending downward from opposite sides of the top wall.

4. The device of claim 1, wherein the top wall, rims and handle portions are formed integrally from a single sheet of material, the rims being bent downwards from opposite sides of the top wall and the handle portions being bent upwards from opposite ends of the top wall.

5. The device of claim 1, wherein the number of holes in the top wall is in the range from 10 to 120.

6. The device of claim 1, wherein the items are tonometer tips and each hole is of predetermined diameter configured to engage a tapered portion of the respective tonometer tip extending partially through the hole.

7. The device of claim 6, wherein the predetermined second distance is selected to provide a space of one to two millimeters above the top of tonometer tips engaged in the holes.

8. The device of claim 6, wherein the predetermined diameter is between a minimum and a maximum diameter of the tapered portion of the tonometer tip.

9. The device of claim 1, wherein the rim portion extends downward from an outermost edge of the top wall.

* * * * *